United States Patent
Mochizuki et al.

(10) Patent No.: US 11,793,874 B2
(45) Date of Patent: Oct. 24, 2023

(54) IMMUNITY-INDUCING AGENT AND PHARMACEUTICAL COMPOSITION CONTAINING SAME

(71) Applicant: The University of Kitakyushu, Kitakyushu (JP)

(72) Inventors: Shinichi Mochizuki, Fukuoka (JP); Kazuo Sakurai, Fukuoka (JP); Hiromi Morishita, Fukuoka (JP)

(73) Assignee: The University of Kitakyushu, Kitakyushu (JP)

( * ) Notice: Subject to any disclaimer, the term of this patent is extended or adjusted under 35 U.S.C. 154(b) by 521 days.

(21) Appl. No.: 16/498,374

(22) PCT Filed: Mar. 20, 2018

(86) PCT No.: PCT/JP2018/011201
§ 371 (c)(1),
(2) Date: Sep. 26, 2019

(87) PCT Pub. No.: WO2018/180819
PCT Pub. Date: Oct. 4, 2018

(65) Prior Publication Data
US 2021/0106678 A1 Apr. 15, 2021

(30) Foreign Application Priority Data
Mar. 30, 2017 (JP) .................. 2017-068276

(51) Int. Cl.
*A61K 39/385* (2006.01)
*A61K 39/39* (2006.01)
*A61K 47/56* (2017.01)

(52) U.S. Cl.
CPC .............. *A61K 39/39* (2013.01); *A61K 47/56* (2017.08)

(58) Field of Classification Search
None
See application file for complete search history.

(56) References Cited

U.S. PATENT DOCUMENTS

| | | |
|---|---|---|
| 2006/0084149 A1 | 4/2006 | Kimura et al. |
| 2015/0191730 A1 | 7/2015 | Levy et al. |
| 2016/0000906 A1 | 1/2016 | Diamond |

(Continued)

FOREIGN PATENT DOCUMENTS

| | | |
|---|---|---|
| EP | 1 142 591 A1 | 10/2001 |
| JP | 2007-70307 A | 3/2007 |

(Continued)

OTHER PUBLICATIONS

English WIPO translation of WO2015118789 (Year: 2022).*

(Continued)

*Primary Examiner* — M Franco G Salvoza
(74) *Attorney, Agent, or Firm* — Christensen O'Connor Johnson Kindness PLLC

(57) ABSTRACT

Disclosed is an immunity-inducing agent having excellent ease of production and high immunostimulatory activity, the immunity-inducing agent comprising, as an active component, a polynucleotide/peptide conjugate in which an antigenic peptide is covalently bound to a single-stranded polynucleotide or polynucleotide derivative. Also disclosed is a pharmaceutical composition comprising said immunity-inducing agent.

14 Claims, 3 Drawing Sheets
Specification includes a Sequence Listing.

(56) References Cited

U.S. PATENT DOCUMENTS

| | | |
|---|---|---|
| 2017/0007695 A1 | 1/2017 | Sakurai et al. |
| 2022/0031839 A1 | 2/2022 | Mochizuki et al. |

FOREIGN PATENT DOCUMENTS

| | | |
|---|---|---|
| JP | 2010-174107 A | 8/2010 |
| JP | 2017500313 A | 1/2017 |
| WO | 01/34207 A1 | 5/2001 |
| WO | 02/072152 A1 | 9/2002 |
| WO | 2015/089114 A1 | 6/2015 |
| WO | 2015/118789 A1 | 8/2015 |
| WO | 2016/152767 A1 | 9/2016 |
| WO | 2017/217531 A1 | 12/2017 |

OTHER PUBLICATIONS

International Search Report dated May 1, 2018, issued in International Application No. PCT/JP2018/011201, filed Mar. 20, 2018, 2 pages.
Khan, S., et al., "Distinct Uptake Mechanisms but Similar Intracellular Processing of Two Different Toll-Like Receptor Ligand-Peptide Conjugates in Dendritic Cells," Journal of Biological Chemistry 282(29):21145-21159, Jul. 2007.
Kramer, K., et al., "Intracellular Cleavable CpG Oligodeoxynucleotide-Antigen Conjugate Enhances Anti-Tumor Immunity," Molecular Therapy 25(1):62-70, Jan. 2017.
Krieg, A.M., "CpG Motifs in Bacterial DNA and Their Immune Effects," Annual Review of Immunology 20:709-760, 2002.
Miyoshi, K., et al., "Polysaccharide-Polynucleotide Complexes. Part 32. Structural Analysis of the Curdlan/Poly (Cytidylic Acid) Complex With Semiempirical Molecular Orbital Calculations," Biomacromolecules 6:1540-1546, 2005.
Mizu, M., et al., "Protection of Polynucleotides Against Nuclease-Mediated Hydrolysis by Complexation With Schizophyllan," Biomaterials 25(15):3109-3116, 2004.
Mizu, M., et al., "A Polysaccharide Carrier for Immunostimulatory CpG DNAs to Enhance Cytokine Secretion," Journal of the American Chemical Society 126:8372-8373, 2004.
Mochizuki, S., and K. Sakurai, "Dectin-1 Targeting Delivery of TNF-α Antisense ODNs Complexed With β-1,3-Glucan Protects Mice From LPS-Induced Hepatitis," Journal of Controlled Release 151:155-161, 2011.
Mochizuki, S., et al., "Complex Consisting of β-Glucan and Antigenic Peptides With Cleavage Site for Glutathione and Aminopeptidases Induces Potent Cytotoxic T Lymphocytes," Bioconjugate Chemistry 28:2246-2253, Jul. 2017.
Mochizuki, S., et al., "Immunization With Antigenic Peptides Complexed With β-Glucan Induces Potent Cytotoxic T-Lymphocyte Activity in Combination With CpG-ODNs," Journal of Controlled Release 220:495-502, Dec. 2015.

Sakurai, K., and S. Shinkai, "Molecular Recognition of Adenine, Cytosine, and Uracil in a Single-Stranded RNA by a Natural Polysaccharide: Schizophyllan," Journal of the Americal Chemical Society 122:4520-4521, 2000.
Sakurai, K., et al., "Polysaccharide-Polynucleotide Complexes. 2. Complementary Polynucleotide Mimic Behavior of the Natural Polysaccharide Schizophyllan in the Macromolecular Complex With Single-Stranded RNA and DNA," Biomacromolecules 2:641-650, 2001.
Shimada, N., et al., "Synthesis and In Vitro Characterization of Antigen-Conjugated Polysaccharide as a CpG DNA Carrier," Bioconjugate Chemistry 17:1136-1140, 2006.
Taniguchi, M., et al., "Microbial DNAs (CpG DNA) and TLR9," Standard Immunology, 2nd ed p. 333, Section 5, 2002.
Tighe, H., et al., "Conjugation of Immunostimulatory DNA to the Short Ragweed Allergen Amb a 1 Enhances Its Immunogenicity and Reduces Its Allergenicity," Journal of Allergy and Clinical Immunology 106(1 Pt 1):124-134, Jul. 2000.
Wagner, H., "Bacterial CpG DNA Activates Immune Cells to Signal Infectious Danger," Advances in Immunology 73:329-368, 1999.
Yamamoto, S., et al., "The Discovery of Immunostimulatory DNA Sequence," Springer Seminars in Immunology 22:11-19, 2000.
International Search Report and Written Opinion, dated Nov. 19, 2019, issued in corresponding International Application No. PCT/JP2019/038090, filed Sep. 27, 2019, 20 pages.
Kramer, K., et al., "Comparative Study of 5'- and 3'-Linked CpG-Antigen Conjugates for the Induction of Cellular Immune Responses", ACS Omega, vol. 2, 227-235, 2017.
Kupihar, Z., et al., "Synthesis and Application of a Novel, Crystalline Phosphoramidite Monomer with Thiol Terminus, Suitable for the Synthesis of DNA Conjugates", Bioorganic & Medicinal Chemistry, vol. 9, 1241-1247, 2001.
Shirota, H., et al., "TLR-9 Agonist Immunostimulatory Sequence Adjuvants Linked to Cancer Antigens", Methods in Molecular Biology, vol. 1139, 337-344, 2014.
Written Opinion dated May 1, 2018, issued in International Application No. PCT/JP2018/011201, filed Mar. 20, 2018, 10 pages.
Motohiko Suzuki, et al., International Immunopharmacology, vol. 7, Issue 1, Jan. 2007, pp. 46-54.
Office Action dated Aug. 23, 2022, issued in corresponding Japanese Application No. 2019-509625, filed Mar. 20, 2018, 7 pages.
Extended European Search Report dated Aug. 24, 2022, issued in corresponding European Application No. 19865489.9, filed Sep. 27, 2019, 2018, 14 pages.
Maurer, T. et al., "CpG-DNA aided cross-presentation of soluble antigens by dendritic cells", European Journal of Immunology 32(8): 2356-2364, Aug. 2, 2022.
Shirota, H. et al., "Regulation of Murine Airway Eosinophilia and Th2 Cells by Antigen-Conjugated CpG Oligodeoxynucleotides as a Novel Antigen-Specific Immunomodulator", The Journal of Immunology, 164:5575-5582, Jan. 1, 2000.

* cited by examiner

IMMUNITY-INDUCING AGENT AND PHARMACEUTICAL COMPOSITION CONTAINING SAME

TECHNICAL FIELD

The present invention relates to a novel immunity-inducing agent for inducing antigenic peptide-specific immune responses, and a pharmaceutical composition comprising the same.

BACKGROUND ART

The basis principle for the prevention of infection through vaccination is that pseudo-infection is artificially established to induce acquired immunity and to elicit antibody production and cell-mediated immunity against particular pathogens. It is known that in acquired immunity, T and B cells, which are responsible for "memory" in immunity, play key roles, and the diversity of antibody variable regions caused by DNA rearrangement enables specific immune responses to numerous numbers of antigens. In contrast, innate immunity, which is mainly mediated by phargocytes such as leukocytes, macrophages and dendritic cells, has been conventionally considered to be a non-specific process of phagocytosis of pathogens and foreign substances, and to merely serve as a "stopgap measure" until acquired immunity is established. However, as a result of advances in studies on the molecular mechanisms of innate immunity, it has been clarified that self/non-self-specific recognition takes place also in innate immunity, and that innate immunity is essential for the establishment of acquired immunity. To be more specific, it has been clarified in recent studies that a family of Toll-like receptors (TLRs), present on antigen-presenting cells such as dendritic cells, macrophages and B cells, can respond to various pathogens, induce cytokine production, and induce acquired immunity through, for example, promotion of differentiation of naïve T cells into Th1 cells, and activation of killer T cells.

Pathogens recognized by the series of TLRs are composed of a wide variety of constituents. One of those constituents is a DNA having a CpG sequence (CpG DNA), which acts as a ligand for TLR9. CpG sequences are nucleotide sequences composed of a basic unit of six nucleotides, in which cytosine (C) and guanine (G) appear side-by-side at the center, and these nucleotide sequences are rare in mammals, and abundant in bacteria. In mammals, most of rare CpG sequences are methylated. Unmethylated CpG sequences, which are rarely observed in mammals, have potent immunostimulatory activity (refer to e.g., NPLs 1 to 3). CpG DNA incorporated into cells by endocytosis is recognized by TLR9 present in phagosome-like vesicles, and can induce strong Th1 responses. Th1 responses suppress Th2-dominated allergic responses, and also have potent antitumor activity. Therefore, CpG DNA is expected to be used not only for infection prevention but also as an adjuvant for allergic and neoplastic diseases (refer to e.g., NPL 4).

However, when CpG DNA is used as an adjuvant in immunotherapy, the problem is how to deliver CpG DNA into target cells while protecting DNA against degradation by nucleases in cytoplasm or plasma, or against non-specific binding to proteins.

The present inventors have focused their attention on polysaccharides having a β-1,3-glucan backbone (hereinafter, sometimes abbreviated as "β-1,3-glucans") as a novel gene carrier, and found that β-1,3-glucans are capable of forming new types of complexes with various nucleic acids including nucleic acid medicines (e.g., antisense DNA, CpG DNA) (refer to e.g., PTLs 1, 2, and NPLs 5 to 7).

It was found that when β-1,3-glucan naturally existing in a triple helix conformation is dissolved in an aprotic polar organic solvent such as dimethyl sulfoxide (DMSO) or in a 0.1 N or higher alkali solution to allow glucan to be dissociated into single strands, then a single-stranded nucleic acid is added, and the solvent is replaced with water or neutralized again, a triple helix complex consisting of one nucleic acid molecule and two β-1,3-glucan molecules is formed. It is considered that in such a triple helix complex, a linkage between the β-1,3-glucan molecules and the nucleic acid molecule is mainly formed by hydrogen bonding and hydrophobic interaction (refer to NPL 8).

The complexation of nucleic acids with β-1,3-glucans, as described above, enabled delivery of nucleic acids into cells while suppressing undesired interactions of nucleic acids with proteins in the body, such as hydrolysis of nucleic acids by nucleases, or non-specific binding of nucleic acids to plasma proteins. The delivery of CpG DNA into cells was succeeded with the use of a complex of β-1,3-glucans and nucleic acids, or a ternary complex containing a protein with antigenicity (refer to e.g., PTLs 3, 4, and NPLs 9 to 11).

However, the aforementioned conventional techniques had some problems as described below. For example, according to the method of producing a β-1,3-glucan/a protein with antigenicity/CpG DNA ternary complex as disclosed in NPL 11, a formyl group is produced on a glucose residue in a side chain of β-1,3-glucan by oxidization with periodic acid, and the formyl group is reacted with an amino group of a peptide with antigenicity (hereinafter, sometimes abbreviated as "antigenic peptide") by reductive amination reaction, so that a complex in which β-1,3-glucan and the antigenic peptide are covalently bound together can be formed. However, this method has a problem of very low yield. In view of such circumstances, according to, for example, the method of producing a β-1,3-glucan/antigenic protein (antigenic peptide)/CpG DNA ternary complex as disclosed in PTL 4, β-1,3-glucan having a formyl group on a side chain thereof and an antigenic peptide are reacted with each other in an aqueous alkaline solution at the same time as, or sequentially followed by, neutralization, so that improvement can be achieved in yield and the reactivity between the formyl group on a side chain of β-1,3-glucan and an amino group of the antigenic peptide. However, since a peptide contains a plurality of amino groups, control of a reaction site is difficult to achieve. Therefore, there is concern that there may occur problems, such as variation in immunogenicity depending on the reaction site of an antigenic peptide, or difficulty in separation and purification due to complexity of reaction mixtures with β-1,3-glucan. Further, the procedure for forming a β-1,3-glucan/antigenic peptide complex based on the formation of covalent bonding is more complicated than that for forming a β-1,3-glucan/DNA complex through hydrogen bonding. From these viewpoints, the method of producing a β-1,3-glucan/antigenic peptide/CpG DNA ternary complex as disclosed in PTL 4 still has problems with ease of production and the like.

In view of such problems, the present inventors have proposed a peptide/β-1.3-glucan complex having excellent ease of production and high immunostimulatory activity, the complex comprising: a polysaccharide having a β-1,3-glucan backbone; and a peptide/polynucleotide conjugate in which an antigenic peptide is covalently bound to a polynucleotide or polynucleotide derivative, wherein the polynucleotide or polynucleotide derivative of the peptide/polynucleotide conjugate is bound via hydrogen bonding to the polysaccharide having a β-1,3-glucan backbone to form a complex having a triple helix structure consisting of one molecular chain of the polynucleotide or polynucleotide derivative and two molecular chains of the polysaccharide having a β-1,3-glucan backbone (refer to PTL 5).

CITATION LIST

Patent Literatures

PTL 1: International Patent Publication No. WO 01/34207
PTL 2: International Patent Publication No. WO 02/072152
PTL 3: Japanese Unexamined Patent Application Publication No. JP 2007-70307
PTL 4: Japanese Unexamined Patent Application Publication No. JP 2010-174107
PTL 5: International Patent Publication No. WO 2015/118789

Non Patent Literatures

NPL 1: Bacterial CpG DNA Activates Immune Cells to Signal Infectious Danger. H. Wagner, *Adv. Immunol.*, 73, 329-368 (1999).
NPL 2: CpG Motifs in Bacterial DNA and Their Immune Effects. M. Krieg, *Annu. Rev. Immunol.*, 20, 709-760 (2002).
NPL 3: The Discovery of Immunostimulatory DNA Sequence. S. Yamamoto, T. Yamamoto, and T. Tokunaga, *Springer Seminars in Immunopathology*, 22, 11-19 (2000).
NPL 4: *Standard Immunology*, 2nd Edition, Igaku-Shoin Ltd., 333 (2002)
NPL 5: Molecular Recognition of Adenine. Cytosine, and Uracil in a Single-Stranded RNA by a Natural Polysaccharide: Schizophyllan. K. Sakurai and S. Shinkai, *J. Am. Chem. Soc.*, 122, 4520-4521 (2000).
NPL 6: Polysaccharide-Polynucleotide Complexes. 2. Complementary Polynucleotide Mimic Behavior of the Natural Polysaccharide Schizophyllan in the Macromolecular Complex with Single-Stranded RNA and DNA. K. Sakurai, M. Mizu and S. Shinkai, *Biomacromolecules*, 2, 641-650 (2001).
NPL 7: Dectin-1 Targeting Delivery of TNF-α Antisense ODNs Complexed with β-1,3-glucan Protects Mice from LPS-induced Hepatitis. S. Mochizuki and K. Sakurai, *J. Control. Release*, 151, 155-161 (2011).
NPL 8: Structural Analysis of the Curdlan/Poly(cytidylic acid) Complex with Semiempirical Molecular Orbital Calculations. K. Miyoshi, K. Uezu. K. Sakurai and S. Shinkai, *Biomacromolecules*, 6, 1540-1546 (2005).
NPL 9. A Polysaccharide Carrier for Immunostimulatory CpG DNAs to Enhance Cytokine Secretion. M. Mizu, K. Koumoto, T. Anada. T. Matsumoto, M. Numata, S. Shinkai, T. Nagasaki and K. Sakurai. *J. Am. Chem. Src.*, 126, 8372-8373 (2004).
NPL 10: Protection of Polynucleotides against Nuclease-mediated Hydrolysis by Complexation with Schizophyllan. M. Mizu, K. Koumoto, T. Kimura. K. Sakurai and S. Shinkai, *Biomaterials*, 25, 15, 3109-3116 (2004).
NPL 11: Synthesis and in Vitro Characterization of Antigen-Conjugated Polysaccharide as a CpG DNA Carrier. N. Shimada, K. J. Ishii, Y. Takeda, C. Coban, Y. Torii, S. Shinkai, S. Akira and K. Sakurai, *Bioconjugate Chem.*, 17 1136-1140 (2006).

SUMMARY OF INVENTION

Technical Problem

However, it was not known whether the peptide/polynucleotide conjugate, which constitutes the peptide/β-1,3-glucan complex disclosed in PTL 5, has per se immunity induction activity.

The present inventors found that the peptide/polynucleotide conjugate, which is not complexed with β-1,3-glucan, has per se high immunity induction activity on its own; and thus, the inventors completed the present invention. Therefore, this invention has as its object to provide an immunity-inducing agent having excellent ease of production and high immunostimulatory activity, and a pharmaceutical composition comprising the same.

Solution to Problem

A first aspect of the present invention in accordance with the aforementioned object solves the problems mentioned hereinabove by providing an immunity-inducing agent comprising, as an active component, a polynucleotide/peptide conjugate in which an antigenic peptide is covalently bound to a single-stranded polynucleotide or polynucleotide derivative.

In the immunity-inducing agent according to the first aspect of the present invention, the antigenic peptide may have an amino acid length of not less than 5 but not more than 30.

In the immunity-inducing agent according to the first aspect of the present invention, the polynucleotide or polynucleotide derivative may have a nucleotide length of not less than 20 but not more than 80.

In the immunity-inducing agent according to the first aspect of the present invention, the polynucleotide or polynucleotide derivative may be polydeoxyadenylic acid.

In the immunity-inducing agent according to the first aspect of the present invention, the polynucleotide or polynucleotide derivative may be polydeoxycytidylic acid, polydeoxythymidylic acid or polydeoxyguanylic acid.

In the immunity-inducing agent according to the first aspect of the present invention, the polynucleotide or polynucleotide derivative may be a polynucleotide derivative in which phosphodiester bonds in DNA or RNA are at least partially substituted with phosphorothioate groups.

In the immunity-inducing agent according to the first aspect of the present invention, it is acceptable that, in the polynucleotide derivative in which phosphodiester bonds in DNA or RNA are at least partially substituted with phosphorothioate groups, not less than 50% of the phosphodiester bonds may be substituted with phosphorothioate groups.

In the immunity-inducing agent according to the first aspect of the present invention, the antigenic peptide and the polynucleotide or polynucleotide derivative, which constitute the polynucleotide/peptide conjugate, may be bound together via covalent bonding produced by any of a cycloaddition reaction between alkyne and an azide derivative, and a reaction between a maleimide group and a thiol group.

In the immunity-inducing agent according to the first aspect of the present invention, the antigenic peptide and the polynucleotide or polynucleotide derivative, which constitute the polynucleotide/peptide conjugate, may be bound together via covalent bonding produced by a reaction between a thiol group of a cysteine residue at the C-terminus of the peptide and a thiol group of a thiol-modified nucleic acid.

In the immunity-inducing agent according to the first aspect of the present invention, a substance having immunostimulatory activity may be further contained as an adjuvant.

In the immunity-inducing agent according to the first aspect of the present invention, the adjuvant may be a polynucleotide or polynucleotide derivative containing a partial nucleotide sequence having immunostimulatory activity.

A second aspect of the present invention solves the problems mentioned hereinabove by providing a pharmaceutical composition comprising the immunity-inducing agent according to the first aspect of the present invention.

Advantageous Effects of Invention

The peptide/polynucleotide conjugate of the present invention can be used as an immunity-inducing agent without being complexed with β-1,3-glucan. Therefore, the peptide/polynucleotide conjugate of this invention is much superior in ease of production over conventional immunity-inducing agents comprising a peptide/β-1,3-glucan complex as an active component. Further, immunity-inducing agents having immunity induction activity against a variety of antigens can be easily designed by combining an antigenic peptide with a polynucleotide or polynucleotide derivative in an appropriate manner.

DESCRIPTION OF EMBODIMENTS

Figure 1:
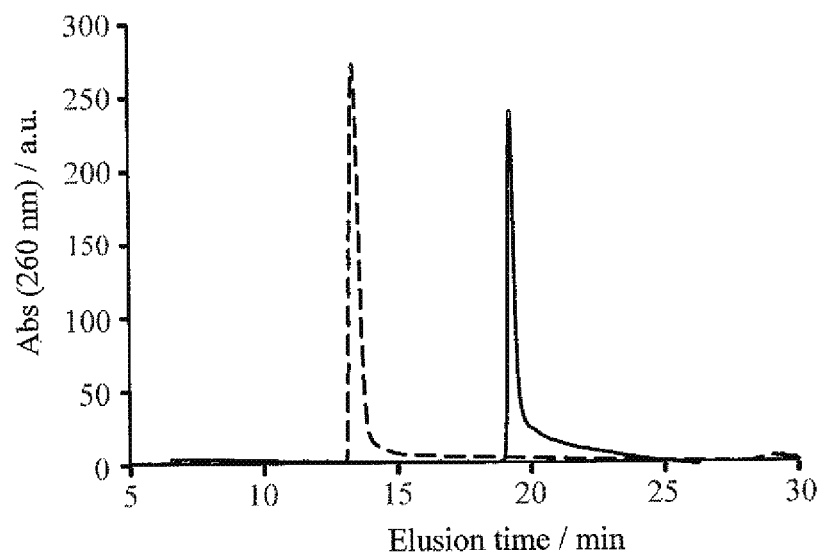
FIG. 1 shows a chromatogram that shows the results of the HPLC fractionation of a solution obtained after the reaction of SPDP-modified dA40(S) with an antigenic peptide.

The immunity-inducing agent according to the first aspect of the present invention (hereinafter, sometimes abbreviated as "immunity-inducing agent") comprises, as an active component, a polynucleotide/peptide conjugate in which an antigenic peptide is covalently bound to a single-stranded polynucleotide or polynucleotide derivative.

The peptide/polynucleotide conjugate is a complex in which an antigenic peptide and a polynucleotide or polynucleotide derivative are bound together via covalent bonding. As the "antigenic peptide", any peptide having any amino acid sequence consisting of any numbers of amino acid residues can be used without particular limitation, as long as it has antigenicity—i.e., it can be recognized as a foreign substance in the immune system of a living body and elicit specific antibody production (induce an immune response). Examples of the antigenic peptide used to produce the peptide/β-1,3-glucan complex according to this aspect of the present invention include proteins responsible for allergies such as food allergy, pathogens such as bacteria and viruses, and proteins originating from tumor cells and the like, as long as they have a partial amino acid sequence that can act as an epitope. The number of amino acid residues constituting the antigenic peptide is not particularly limited as long as they can act as an epitope, but the number of amino acid residues commonly ranges from 5 to 30, and most commonly ranges approximately from 8 to 17.

The antigenic peptide can be obtained using any known method, such as enzymatic degradation of a protein of origin, or peptide synthesis. Further, the amino acid sequence of the antigenic peptide can be determined using any known method such as epitope analysis using a peptide array.

As the polynucleotide or polynucleotide derivative to which the antigenic peptide is bound, any polynucleotide or polynucleotide derivative having any nucleotide sequence consisting of any numbers of nucleotides can be used without particular limitation. Specific examples of the polynucleotide include polyadenylic acid (poly A), polycytidylic acid (polyC), polydeoxyadenylic acid (poly(dA)), polydeoxythymidylic acid (poly(dT)), and polydeoxyguanylic acid (poly(dG)). The number of nucleotides constituting the polynucleotide is not particularly limited, but it is preferred that the polynucleotide contain a repetitive sequence found in any of polyadenylic acid (poly A), polycytidylic acid (polyC), polydeoxyadenylic acid (poly(dA)), polydeoxythymidylic acid (poly(dT), and polydeoxyguanylic acid (poly (dG)) which have a high binding capacity for β-1,3-glucan. The number of nucleotides is preferably not less than 10, more preferably ranges from 20 to 80, still more preferably ranges from 30 to 80.

Since the polynucleotide is susceptible to degradation by nuclease in the living body, a polynucleotide derivative may be used instead of the polynucleotide with the aim of enhancement of stability in the living body. Examples of the polynucleotide derivative include those derivatives in which the hydroxyl groups at the 2' position of a ribonucleotide are completely or partially substituted with fluorine or methoxy groups, and those derivatives in which the phosphodiester groups in a polyribonucleotide (RNA) or a polydeoxyribonucleotide (DNA) are completely or partially substituted with phosphorothioate groups. In the case of those derivatives in which the phosphodiester groups in a polyribonucleotide or a polydeoxyribonucleotide are partially substituted with phosphorothioate groups, it is preferred that not less than 50% of the phosphodiester bonds be substituted with phosphorothioate groups. The positions of phosphodiester groups to be substituted with phosphorothioate groups are not particularly limited. Two or more consecutive phosphodiester groups may be substituted, or phosphodiester groups may be substituted so as to ensure that phosphorothioate groups are not adjacent to each other.

The polynucleotide or polynucleotide derivative can be bound to any of the N-terminus, C-terminus, and side chains of the antigenic peptide, but it is preferred that the polynucleotide or polynucleotide derivative be bound toward the N-terminus of the antigenic peptide. The polynucleotide or polynucleotide derivative and the antigenic peptide may be directly bound together by a reaction between appropriate reactive functional groups, or may be bound together through an appropriate spacer. As the reactive functional groups, any functional groups present in the antigenic peptide and the polynucleotide or polynucleotide derivative may be used as they are or after being activated by chemical modification, or any appropriate reactive functional groups may be introduced separately. Further, it is acceptable that a region toward the 5' end, or the 3' end, of the polynucleotide or polynucleotide derivative may be bound to the antigenic peptide.

One preferred example of the peptide/polynucleotide conjugate has a structure represented by formula (A) below, in which a region toward the N-terminus of a peptide is bound to a region toward the 5' end of phosphorothioated polydeoxyadenylic acid (a polynucleotide derivative in which phosphodiester groups in polyA are substituted with phosphorothioate groups).

[Antigenic peptide]-X-(dA(S))x     (A)

In formula (A), dA(S) represents phosphorothioated deoxyadenylic acid, and x is an integer of, for example, not less than 20 but not more than 80. X represents a spacer, or a functional group formed by a reaction between reactive functional groups. Examples of the spacer include alkyl group, and polyethylene glycol (PEG). Examples of a combination of reactive functional groups include a combination of reactive functional groups used for immobilization of a biomolecule on a biochip surface. More specific examples thereof are detailed below.

(a) Alkyne and an Azide

Alkyne and an azide form a 1,2,3-triazole ring through a cycloaddition reaction (Huisgen reaction) as illustrated below. These compounds, which are stable functional groups capable of being introduced into many organic compounds including biomolecules, react with each other rapidly and nearly quantitatively even in a solvent including water, and generate no unnecessary wastes with little side reaction; thus, they are widely used predominantly in so-called "click chemistry" reactions in the field of biochemistry. An alkyne derivative and an azido group can be introduced into an antigenic peptide or a polynucleotide or polynucleotide derivative using any known method. As for the alkyne derivative, those derivatives having a reactive functional group are easily available, such as propargyl alcohols or propargyl amines. By being reacted directly with a reactive functional group such as carboxyl group or hydroxyl group, or reacted with carbonyldiimidazole or the like, such an alkyne derivative can be introduced into an antigenic peptide or a polynucleotide or polynucleotide derivative, through amide bonding, ester bonding, urethane bonding, or other bonding formed by the reaction. The azido group can also be introduced into an antigenic peptide or a polynucleotide or polynucleotide derivative using any known method. Additionally, the Huisgen reaction is performed in the presence of a copper catalyst. However, since antigenic peptides, and polynucleotide derivatives in which the phosphodiester groups are substituted with sulfur-containing functional groups such as phosphorothioate groups, contain sulfur atoms coordinating to a copper ion, there may occur a deterioration of the catalytic activity of copper. Thus, it is preferred to add an excess amount of copper for the purpose of increasing the rate of reaction.

[Chem. 1]

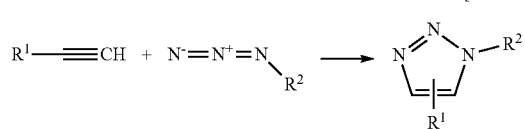

(b) Maleimide or Vinyl Sulfone and a Thiol Group

Maleimide or vinyl sulfone, which has double bonds adjacent to an electron-withdrawing carbonyl or sulfone group, produces a stable thioether derivative at a near-neutral pH through an addition reaction (Michael addition reaction) with a thiol group as illustrated below. Since maleimide and vinyl sulfone derivatives containing a suitable spacer are commercially available, it is easy to introduce such a functional group into an antigenic peptide or a polynucleotide or polynucleotide derivative. In the case of introduction of a thiol group into an antigenic peptide, when the antigenic peptide contain cysteine, a thiol group of the side chain of the cysteine residue can be utilized. However, since cysteine is an amino acid with low abundance ratio, an antigenic peptide having cysteine introduced toward the N-terminus thereof is used. As the polynucleotide or polynucleotide derivative containing a thiol group, a thiolated polynucleotide in which the hydroxyl group at the 5' end is converted to a thiol group is used.

[Chem. 2]

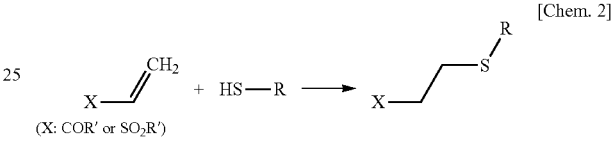

(c) Thiol Group of a Cysteine Side Chain and Thiol Group of a Thiolated Polynucleotide As mentioned above, a thiol group of the cysteine side chain of an antigenic peptide having cysteine introduced toward the N-terminus thereof is reacted with a thiol group of a thiolated polynucleotide to form a disulfide group. Since the disulfide bonding is cleaved in the presence of a reducing agent, this bonding is inferior in stability over those mentioned in the previous sections. The introduction of a thiol group into a polynucleotide or polynucleotide derivative can be performed using any known method. One specific example of such a method is a reaction of an aminated polynucleotide or polynucleotide derivative with an N-succinimidyl ester of ω-(2-pyridyldithio)fatty acid as illustrated below.

[Chem. 3]

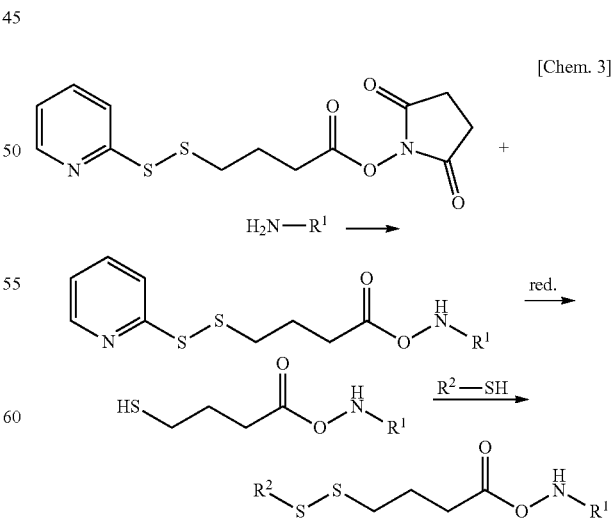

A pharmaceutical composition comprising the immunity-inducing agent can be produced by using, in addition to a peptide/polynucleotide conjugate as an active component, any known components (any carriers, excipients and additives acceptable for pharmaceutical purposes) and by using any known pharmaceutical formulation method. For example, the pharmaceutical composition can take the form of tablet, suppository, capsule, syrup, microcapsule such as nanogel, injectable solution such as sterile solution or suspension, aerosol, spray, or the like.

The pharmaceutical composition may further comprise an adjuvant as a substance having immunostimulatory activity. The adjuvant is selected as appropriate depending on the type of an antigenic peptide or the like introduced into a peptide/polynucleotide conjugate. For example, the adjuvant can be CpG DNA or the like, or can be a polynucleotide/β-1,3-glucan complex, as disclosed in International Patent Publication No. WO 2015/118789, which is formed by binding a polynucleotide or polynucleotide derivative containing a partial nucleotide sequence having immunostimulatory activity to a polysaccharide having a β-1,3-glucan backbone via hydrogen bonding, and which has a triple helix structure consisting of one molecular chain of the polynucleotide or polynucleotide derivative and two molecular chains of the polysaccharide having a β-1,3-glucan backbone.

The pharmaceutical composition can be administered to a human or a warm-blooded animal (e.g., mouse, rat, rabbit, sheep, pig, cow, horse, chicken, cat, dog, monkey) by any of oral and parenteral routes. Examples of parenteral routes include subcutaneous, intracutaneous and intramuscular injections, intraperitoneal administration, drip infusion, and spray into nasal mucosa or pharyngeal region.

The dose of a peptide/polynucleotide conjugate as an active component differs according to activity, the disease to be treated, the type, body weight, sex and age of an animal to be medicated, the severity of a disease, administration method, and/or the like. As an example, in the case of medication of an adult individual with a body weight of 60 kg, the daily dose for oral administration is generally in the range of about 0.1 to about 100 mg, preferably about 1.0 to about 50 mg, more preferably about 1.0 to about 20 mg, and the daily dose for parenteral administration is generally in the range of about 0.01 to about 30 mg, preferably about 0.1 to about 20 mg, more preferably about 0.1 to about 10 mg. When the pharmaceutical composition is administered to other animals, the dose to be used for such animals is calculated by converting the aforementioned dose into a dose per unit body weight and multiplying the dose per unit body weight by the weight of an animal to be medicated.

The pharmaceutical composition can be used as a vaccine or the like for the purpose of the treatment and prevention of infectious diseases caused by infection with pathogens such as bacteria and viruses, and tumors such as cancers, through activation of immunity.

EXAMPLES

Next, the following describes working examples conducted to confirm the actions and effects of the present invention.

Example 1: Preparation of a dA40(S)-Peptide Conjugate

One mol of amino group-modified dA40(S) (a 40-mer of deoxyadenosine in which the phosphodiester groups are substituted with phosphorothioate groups) was mixed with 30 mol of succinimidyl 6-[3'-(2-pyridyldithio)-propionamido]hexanoate (LC-SPDP) in a phosphate buffer (pH 8.0). After being left to stand at 40° C. for 3 hours, the mixture was purified using a NAP-5 column to yield SPDP-modified dA40(S).

One mol of the SPDP-modified dA40(S) was mixed with 25 mol of an ovalbumin (OVA)-derived antigenic peptide (with an amino acid sequence of SIINFEKL (SEQ ID NO: 1)) in 30% N,N-dimethylformamide (DMF). After being left to stand at 40° C. for 3 hours, the mixture was fractionated by HPLC to afford a dA-peptide conjugate. HPLC was performed under the following gradient conditions using 0.1 M triethylammonium acetate (TEAA; pH 7.0) and acetonitrile as solvents A and B, respectively, and the column ZORBAX Eclipse Plus C18.

0 min. A: 90% B: 10%
to 25 min. A: 70% B: 30%
to 30 min. A: 0% B: 100%

The results of the HPLC fractionation of the solution obtained after the reaction of the SPDP-modified dA40(S) with the antigenic peptide are shown in FIG. 1. Detection was performed by monitoring the absorption at 260 nm for dA40(S). It can be observed that the elution time of the peak of fractionated dA40(S) was delayed. This is considered to be because the elution time became later since dA40(S) was bound to the hydrophobic peptide. Further, in the chromatogram obtained from the fractionation, no peak for unreacted dA40(S) is observed, and only the peak for the dA40(S)-peptide conjugate is detected, thus, this indicates that the dA40(S)-peptide conjugate of interest was obtained in high purity.

Figure 2:
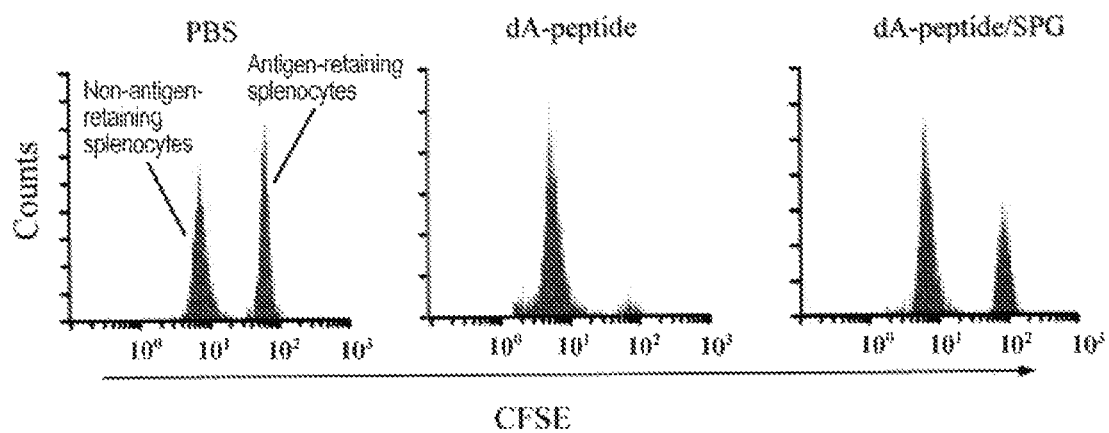
FIG. 2 shows the results of the flow cytometric analysis performed in Example 2.

Example 2: Evaluation of Induction of Cytotoxic T Lymphocytes by dA40(S)-Peptide Conjugate The dA40(S)-peptide conjugate as an antigen, and a CpG-dA/SPG complex (refer to International Patent Publication No. WO 2015/118789) as an adjuvant were administered intracutaneously to mice (C57BL/6 mice ♂, 7 weeks old)) (one time). After one week of administration, splenocytes were isolated from other mice of the same strain not receiving administration, and divided into two groups. To one group, an ovalbumin (egg albumin, OVA)-derived antigenic peptide (with a peptide sequence of SIINFEKL (SEQ ID NO. 1)) as an antigen was added, and the mixture was left to stand for 90 minutes to prepare antigen-retaining splenocytes. The other group of splenocytes not receiving addition of the peptide was regarded as non-antigen-retaining splenocytes. Both of the antigen-retaining splenocytes and the non-antigen-retaining splenocytes were fluorescently modified with carboxyfluorescein succinimidyl ester (CFSE). In this process, the concentration of CFSE was varied such that the fluorescence intensity of the antigen-retaining splenocytes was higher than that of the non-antigen-retaining splenocytes. The same numbers of the antigen-retaining and non-antigen-retaining splenocytes were mixed together, and administered via tail vain to the mice receiving antigen and adjuvant administration, after one week of administration. The dose of the dA40(S)-peptide conjugate was 20 ng in terms of peptide, and the dose of the adjuvant was 30 μg in terms of CpG-DNA After the lapse of 24 hours from the tail vein administration, splenocytes were isolated from the mice, and evaluated for induction of cytotoxic T lymphocytes through flow cytometric quantification of the percentages of antigen-retaining and non-antigen-retaining splenocytes. The results of the flow cytometric analysis are shown in FIG. 2. For comparison's sake, other mice were administered either PBS (phosphate-buffered saline) or a dA40(S)-peptide conjugate/

SPG complex in which the dA40(S)-peptide conjugate has been complexed with SPG, instead of the dA40(S)-peptide conjugate, and served as control groups. The results of the flow cytometric analysis conducted for the control groups under the same conditions are also shown in FIG. 2.

The splenocytes collected from the mice administered PBS contained the same numbers of antigen-retaining and non-antigen-retaining splenocytes, while antigen-retaining splenocytes alone disappeared from the splenocytes collected from the mice administered the dA40(S)-peptide conjugate. This indicates that administration of the dA40 (S)-peptide conjugate and the CpG-dA/SPG complex as an adjuvant resulted in induction of a peptide antigen-specific immune response. It was also found that the effect of this administration was higher than that of administration of the dA40(S)-peptide conjugate/SPG complex (antigen-retaining splenocytes were detected in the splenocytes collected from the mice administered the dA40(S)-peptide conjugate/SPG complex).

Example 3: Dependence on the Nucleotide Length of dA(S) Used in a Conjugate

Different conjugates were prepared by the same procedure as in Example 1, except that the nucleotide length of dA(S) to be conjugated was changed from 40 to 20 or 30. Mice were immunized with the different conjugates comprising different lengths of DNA, and then, as in the previous example, administered a mixture of antigen-retaining and non-antigen-retaining splenocytes via tail vein and evaluated for induction of cytotoxic T lymphocytes through flow cytometric quantification of the percentages of antigen-retaining and non-antigen-retaining splenocytes.

Figure 3:
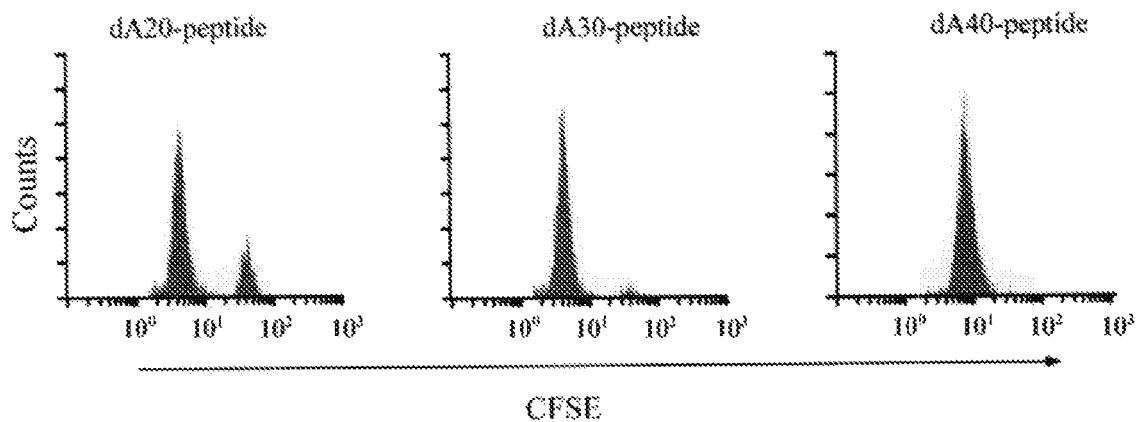
FIG. 3 shows the results of the flow cytometric analysis performed in Example 3.

The results of the flow cytometric analysis are shown in FIG. 3. It was found that in the case where the nucleotide length of dA(S) was shorten to 30, antigen-retaining splenocytes completely disappeared. It was found that in the case where the nucleotide length of dA(S) was shorten to 20, the activity of peptide-specific cytotoxic T lymphocytes was induced, though the inducing effect diminished slightly.

Example 4: Dependence on the Dose of a dA30(S)-Peptide Conjugate

Mice were immunized with varied peptide doses with the nucleotide length of dA(S) to be conjugated being fixed to 30. As in Example 2, the mice were evaluated for induction of cytotoxic T lymphocytes through flow cytometric quantification of the percentages of antigen-retaining and non-antigen-retaining splenocytes in the splenocytes collected from the mice administered via tail vein.

Figure 4:
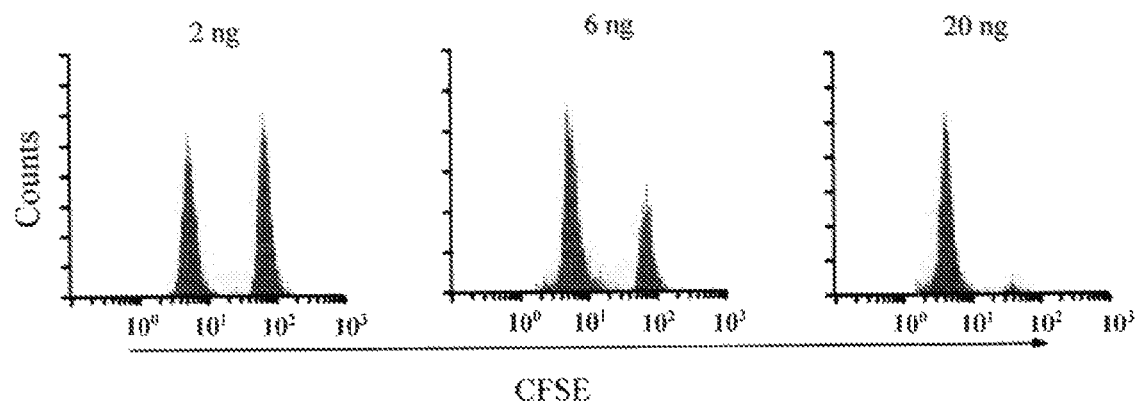
FIG. 4 shows the results of the flow cytometric analysis performed in Example 4.

The results of the flow cytometric analysis are shown in FIG. 4. It was found that as the dose of a dA30(S)-peptide conjugate was decreased to less than 20 ng in terms of peptide, the effect of the conjugate diminished gradually. In general, peptide immunization requires administration of a peptide dose of several micrograms, and immunization with a dA30(S)-peptide conjugate/SPG complex requires administration of a peptide dose of at least 100 ng. However, according to the present invention, the peptide dose was successfully reduced to a hundredth to a thousandth.

Example 5: Dependence on the Chemical Structure of DNA in a Peptide/Nucleotide Conjugate The dA used to prepare conjugates in the previous examples was a DNA containing phosphorothioate bonds. In this example, in order to investigate how cytotoxic T lymphocyte induction activity changes when the phosphorothioate bonds are partially or completely substituted with phosphodiester bonds, evaluation of induction of cytotoxic T lymphocytes was made while varying the content of phosphorothioate groups. The following three types of dA30 were prepared: dA30 (All PS), in which the phosphodiester groups are completely substituted with phosphorothioate groups; dA30 (⅓ PS), in which a third of the phosphodiester groups are substituted with phosphorothioate groups; and dA30 (All PO), which contain no phosphorothioate groups. According to the same procedure as in Example 1, peptide conjugates were prepared and immunized to mice. As in Example 2, evaluation of induction of cytotoxic T lymphocytes was made through flow cytometric quantification of the percentages of antigen-retaining and non-antigen-retaining splenocytes collected from the mice administered via tail vein.

Figure 5:
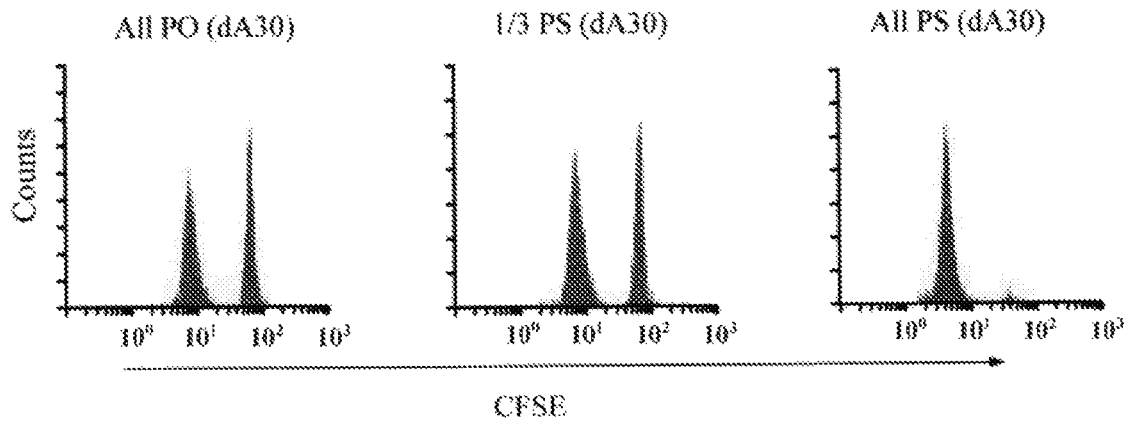
FIG. 5 shows the results of the flow cytometric analysis performed in Example 5.

The results of the flow cytometric analysis are shown in FIG. 5. It was found that cytotoxic T lymphocyte induction activity decreased with a decrease in the percentage of phosphorothioate bonds. This result suggests a deep relationship of the character of phosphorothioate bonds with cell uptake.

Example 6: Effect of an Antigenic Peptide Other than Ovalbumin

The antigenic peptide used in the previous examples was an ovalbumin-derived peptide. In this example, evaluation was made while replacing this peptide with a different antigenic peptide sequence. According to the same procedure as in Example 1, except that the murine melanoma-associated antigen TRP2 (SVYDFFVWL) (SEQ ID NO: 2) was selected as an antigenic peptide, a peptide conjugate was prepared and immunized to mice. Then, as in Example 2, evaluation of induction of cytotoxic T lymphocytes was made through flow cytometric quantification of the percentages of antigen-retaining and non-antigen-retaining splenocytes collected from the mice administered via tail vein.

Figure 6:
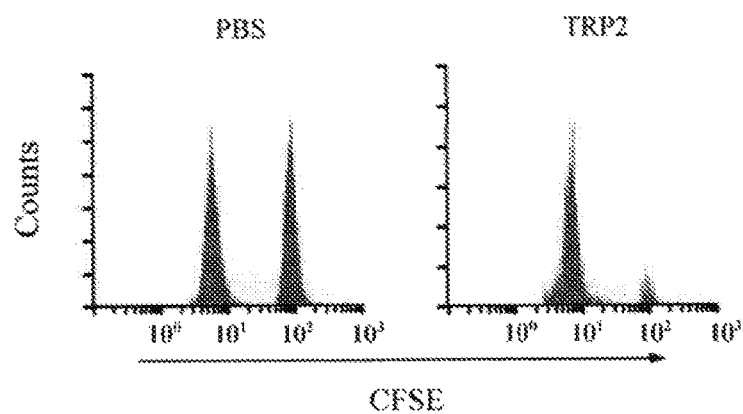
FIG. 6 shows the results of the flow cytometric analysis performed in Example 6.

The results of the flow cytometric analysis are shown in FIG. 6. It was found that comparable cytotoxic T lymphocyte induction activity was exhibited against the TRP2 peptide. It was found that a peptide conjugate prepared with a highly antigenic peptide enables effective induction of peptide-specific immune responses.

Example 7: Dependence on the Sequence of DNA in a Peptide/Nucleotide Conjugate

The nucleic acid used to prepare conjugates in the previous examples was dA. In this example, in order to investigate how cytotoxic T lymphocyte induction activity changes when this sequence is replaced with polydeoxycytidylic acid (dC) or polydeoxythymidylic acid (dT) evaluation was made while varying the sequence of nucleic acid. The following three types of nucleic acids were prepared: dA40, dC40, and dT40. According to the same procedure as in Example 1, peptide conjugates were prepared and immunized to mice. Then, as in Example 2, evaluation of induction of cytotoxic T lymphocytes was made through flow cytometric quantification of the percentages of antigen-retaining and non-antigen-retaining splenocytes collected from the mice administered via tail vein.

Figure 7:
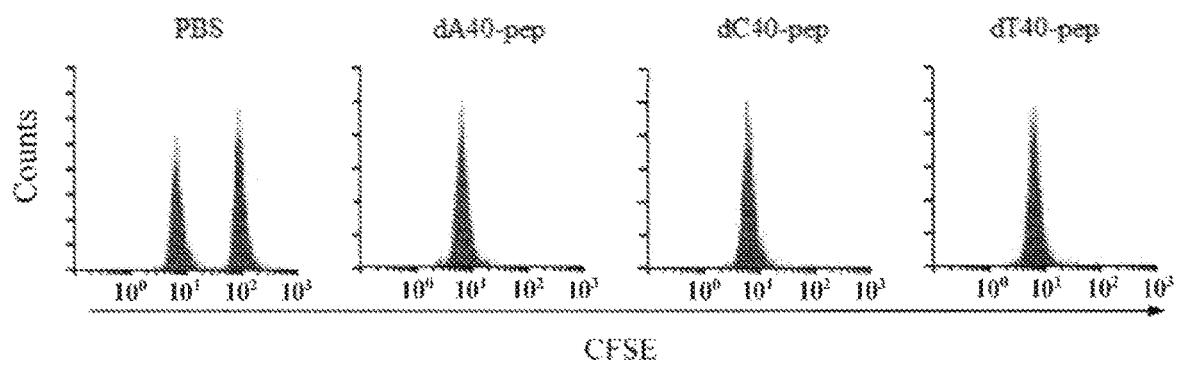
FIG. 7 shows the results of the flow cytometric analysis performed in Example 7.

The results of the flow cytometric analysis are shown in FIG. 7. It was found that even when the nucleic acid sequence was changed to dC or dT, no influence was observed on cytotoxic T lymphocyte induction activity. This result revealed that induction of cytotoxic T lymphocytes by a peptide/nucleotide conjugate does not depend on the sequence of DNA.

In the present invention, various embodiments and modifications are possible without departing from the broad spirit and scope of this invention. The embodiments presented above are intended to be illustrative and not limiting of this invention. In other words, the scope of this invention is defined not by the embodiments presented, but by the attached claims. Further, various modifications made within the scope of claims and within the doctrine of equivalents thereof are regarded as being within the scope of this invention.

The present application is based on Japanese Patent Application No. JP 2017-68276 filed on Mar. 30, 2017, and incorporates the description, claims, drawings and abstract of said application. The disclosures of said application are incorporated herein by reference in their entirety.

6. The immunity-inducing agent according to claim 1, wherein the antigenic peptide and the polynucleotide or polynucleotide derivative, which constitute the polynucleotide/peptide conjugate, are bound together via covalent bonding produced by any of a cycloaddition reaction between alkyne and an azide derivative, and a reaction between a maleimide group and a thiol group.

7. The immunity-inducing agent according to claim 1, wherein the antigenic peptide and the polynucleotide or polynucleotide derivative, which constitute the polynucleotide/peptide conjugate, are bound together via covalent bonding produced by a reaction between a thiol group of a cysteine residue at the C-terminus of the peptide and a thiol group of a thiol-modified nucleic acid.

8. The immunity-inducing agent according to claim 1, further comprising a substance having immunostimulatory activity as an adjuvant.

The invention claimed is:

1. An immunity-inducing agent comprising, as an active component, a polynucleotide/peptide conjugate in which an antigenic peptide is covalently bound to a single-stranded polynucleotide or polynucleotide derivative, wherein the polynucleotide or polynucleotide derivative is a polydeoxyadenylic acid, and wherein the polynucleotide or polynucleotide derivative is not complexed with β-1,3-glucan.

2. The immunity-inducing agent according to claim 1, wherein the antigenic peptide has an amino acid length of not less than 5 but not more than 30.

3. The immunity-inducing agent according to claim 1, wherein the polynucleotide or polynucleotide derivative has a nucleotide length of not less than 20 but not more than 80.

4. The immunity-inducing agent according to claim 1, wherein the polynucleotide or polynucleotide derivative is a polynucleotide derivative in which phosphodiester bonds are at least partially substituted with phosphorothioate groups.

5. The immunity-inducing agent according to claim 4, wherein, in the polynucleotide derivative in which phosphodiester bonds are at least partially substituted with phosphorothioate groups, not less than 50% of the phosphodiester bonds are substituted with phosphorothioate groups.

9. The immunity-inducing agent according to claim 8, wherein the adjuvant is a polynucleotide or polynucleotide derivative containing a partial nucleotide sequence having immunostimulatory activity.

10. A pharmaceutical composition comprising the immunity-inducing agent according to claim 1.

11. The immunity-inducing agent according to claim 1, wherein
the antigenic peptide has an amino acid length of not less than 5 but not more than 30;
the polynucleotide or polynucleotide derivative has a nucleotide length of not less than 20 but not more than 80;
the polynucleotide or polynucleotide derivative is a polynucleotide derivative in which phosphodiester bonds are at least partially substituted with phosphorothioate groups, wherein in said polynucleotide derivative, not less than 50% of the phosphodiester bonds are substituted with phosphorothioate groups;
the antigenic peptide and the polynucleotide or polynucleotide derivative, which constitute the polynucleotide/peptide conjugate, are bound together via covalent bonding produced by any of a cycloaddition reaction between alkyne and an azide derivative, and a reaction between a maleimide group and a thiol group; and further comprising a substance having immunostimulatory activity as an adjuvant.

12. The immunity-inducing agent according to claim 1, wherein
the antigenic peptide has an amino acid length of not less than 5 but not more than 30;
the polynucleotide or polynucleotide derivative has a nucleotide length of not less than 20 but not more than 80;
the polynucleotide or polynucleotide derivative is a polynucleotide derivative in which phosphodiester bonds are at least partially substituted with phosphorothioate groups, wherein, in said polynucleotide derivative, not less than 50% of the phosphodiester bonds are substituted with phosphorothioate groups;
the antigenic peptide and the polynucleotide or polynucleotide derivative, which constitute the polynucleotide/peptide conjugate, are bound together via covalent bonding produced by a reaction between a thiol group of a cysteine residue at the C-terminus of the peptide and a thiol group of a thiol-modified nucleic acid; and
further comprising a substance having immunostimulatory activity as an adjuvant.

13. A pharmaceutical composition comprising the immunity-inducing agent according to claim 11.

14. A pharmaceutical composition comprising the immunity-inducing agent according to claim 12.

* * * * *

```
                          SEQUENCE LISTING

<160> NUMBER OF SEQ ID NOS: 2

<210> SEQ ID NO 1
<211> LENGTH: 8
<212> TYPE: PRT
<213> ORGANISM: Gallus gallus domesticus

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Mus musculus

<400> SEQUENCE: 2

Ser Val Tyr Asp Phe Phe Val Trp Leu
1               5
```